United States Patent [19]

Lashier et al.

[11] Patent Number: 5,210,361
[45] Date of Patent: May 11, 1993

[54] ALLYL AKLALI METAL ALKENE ADDITION PROCESS

[75] Inventors: Mark E. Lashier; Henry L. Hsieh, both of Bartlesville, Okla.

[73] Assignee: Phillips Petroleum Company, Bartlesville, Okla.

[21] Appl. No.: 769,278

[22] Filed: Oct. 1, 1991

[51] Int. Cl.$^5$ .......................... C07C 2/26; C07C 2/34; B01J 31/00
[52] U.S. Cl. .................... 585/511; 585/510; 585/516; 502/152; 502/153
[58] Field of Search ................. 585/510, 511, 516; 502/152, 153

[56] References Cited

U.S. PATENT DOCUMENTS

| | | | |
|---|---|---|---|
| 3,041,312 | 6/1962 | Boyd | 585/511 |
| 3,223,742 | 12/1965 | Eberhardt | |
| 3,251,895 | 5/1966 | Wilkes | 585/516 |
| 3,404,194 | 10/1968 | Crain et al. | 585/511 |
| 3,607,851 | 9/1971 | Forman | |
| 4,535,135 | 8/1985 | Lecolier et al. | 585/511 |
| 4,855,523 | 8/1989 | Stevens et al. | 585/511 |

FOREIGN PATENT DOCUMENTS 933700 8/1963 United Kingdom .

OTHER PUBLICATIONS

Wilks, "Dimerization of Propylene to 4-Methyl-1-Pentene with Catalysts Divided from Potassium", Proceedings 7th World Petroleum Congress, vol. 5, pp. 299-308 (1968).
J. Polymer Science Part A-1 7: pp. 461-469 (1969).
Tetrahedron Letters No. 2 pp. 257-262 (1966).

Primary Examiner—Patrick P. Garvin
Assistant Examiner—E. D. Irzinski
Attorney, Agent, or Firm—Carl D. Corvin

[57] ABSTRACT

A process is provided comprising contacting a hydrocarbyl lithium with an alkali metal hydrocarbyloxide in the presence of propylene. Optionally, a catalytic support is used during said contacting. Optionally, at least one other alpha-olefin is present during said contacting.

In another embodiment a process is provided comprising: (a) contacting a hydrocarbyl lithium with an alkali metal hydrocarbyloxide in the presence of propylene; and thereafter (b) recovering an allyl alkali metal compound; and thereafter (c) contacting said allyl alkali metal compound with at least one alpha-olefin. Optionally, a catalytic support is also used during steps a, b, and c.

32 Claims, No Drawings

ALLYL AKLALI METAL ALKENE ADDITION PROCESS

BACKGROUND OF THE INVENTION

This invention relates to a process for the addition of an alkene to an allyl alkali metal compound.

Alkylation, in general, is a process involving the addition of an alkyl group. Specifically, the term is used in the art to apply to various methods, including both thermal and catalytic processes, for bringing about the union of paraffinic hydrocarbons with olefins. Alkylation reactions are important throughout synthetic organic chemistry. For example, the process is especially effective in yielding gasolines of high octane number and low boiling range which are useable as aviation fuels.

Dimerization, in general, is a process involving the addition of an alkene to another alkene which has the same molecular structure. Dimerization processes are important in organic chemistry for a variety of reasons. For example, dimerization reactions are used to form higher alpha olefins from lower alpha olefins thereby providing higher molecular weight monomers which can then be polymerized. For example, propylene can be dimerized to form 4-methyl-1-pentene which in turn can be polymerized into poly(4-methyl-1-pentene). Currently, a preferred method in the art to perform dimerization reactions involves using an alkali metal on an alkali metal carbonate. However, these alkali metal/alkali metal carbonate catalyst systems tend to suffer from severe degradation which can lead to reactor plugging and shorter catalyst life. Additionally, it has been theorized that the conversion of the alkali metal to an active species can result in the expansion of the alkali metal in the alkali metal carbonate to the point that the catalytic system starts to break down. Therefore, methods to produce a catalytically active species without the use of an elemental alkali metal would be both scientifically and economically valuable.

SUMMARY OF THE INVENTION

It is an object of this invention to provide an improved alkene addition process.

It is another object of this invention to provide an improved dimerization process.

These and other objects of this invention will become apparent to those skilled in the art from the following detailed description of the invention.

In accordance with one embodiment of this invention, a process is provided comprising contacting a hydrocarbyl lithium with an alkali metal hydrocarbyloxide in the presence of propylene. Optionally, a catalytic support is used during said contacting. Optionally, at least one other alpha-olefin is present during said contacting.

In another embodiment a process is provided comprising: (a) contacting a hydrocarbyl lithium with an alkali metal hydrocarbyloxide in the presence of propylene; and thereafter (b) recovering an allyl alkali metal compound; and thereafter (c) contacting said allyl alkali metal compound with at least one alpha-olefin. Optionally, a catalytic support present during steps a, b, and c.

DETAILED DESCRIPTION OF THE INVENTION

In general, the processes in this invention comprise contacting an alpha-olefin with an allyl alkali metal compound to form an addition product.

Alpha Olefin Reactants

The alpha olefin reactants that are applicable for use in this invention can be categorized by the following:

1) the alpha-olefin should have at least one double bond attached to the first carbon atom;
2) the alpha olefin should have between 2 and 20 carbon atoms inclusive in the molecule;
3) the alpha olefin cannot contain any oxygen atoms, acid groups, or conjugated double bonds;
4) the alpha olefin can be linear or branched.

Although not wanting to be bound by theory it has been theorized that those alpha olefins which have the above characteristics have the ability to form a semi-stable resonance group with an alkali metal. Examples of suitable alpha-olefins useful in this invention include, but are not limited to, ethylene, propylene, 1-butene, isobutylene, 3-methyl-1-butene, 1-pentene, 3-methyl-1-pentene, 4-methyl-1-pentene, 1-hexene, 3-ethyl-1-hexene, 1-octene, 1-decene, or mixtures thereof.

Allyl Alkali Metal Compound

The organometallic compounds useful in this invention are those compounds composed of an allyl group and an alkali metal. Specifically, these compounds are allyl lithium, allyl sodium, allyl potassium, allyl cesium, and allyl rubidium. It has been theorized that these particular compounds form substantially stable resonance groups useful for adding alkenes too.

Procedures to Make the Allyl Alkali Metal Compound

It is well known in the art that allyl lithium can be formed by the reaction of allyl chloride or allyl bromide with metallic lithium in order to form the allyl lithium compound. However, in order to make allyl alkali metal groups other than allyl lithium it is necessary to use a different process. In general, the process of forming allyl alkali metal compounds, other than allyl lithium, is accomplished by contacting an hydrocarbyl lithium compound with an alkali metal hydrocarbyloxide in the presence of propylene. This reaction yields, in general, a hydrocarbon, lithium hydrocarbyloxide, and an allyl alkali metal compound.

The hydrocarbyl lithium used in the above reaction can be characterized as follows. The hydrocarbyl group can be a linear or branched alkyl or aryl and can contain from 1 to 20 and most preferably from 2 to 12 carbon atoms in the molecule. However, the hydrocarbyl group must be non-reactive in an alkene addition reaction. This means, in general, that the hydrocarbyl group must not contain any oxygen atoms, nor any acid groups, which could interfere with the reaction. The mole ratio of hydrocarbyl lithium to alkali metal hydrocarbyloxide varies from a ratio of 20:1 down to 1:1. Examples of suitable hydrocarbyl lithium compounds useful in this invention are methyl lithium, ethyl lithium, propyl lithium, butyl lithium, pentyl lithium, and hexyl lithium.

The alkali metal hydrocarbyloxide can be characterized by the following. The hydrocarbyloxide can be a linear or branched alkyl or aryl and can contain from 1 to 20 and most preferably from 2 to 12 carbon atoms in the molecule. It is also important that this hydrocarbyloxide be nonreactive in alkene addition reactions. This means, in general, that the hydrocarbyloxide cannot contain any oxygen atoms, besides the one connecting to the alkali metal, nor any acid groups, which could interfere with the reaction. Examples of suitable alkali metal hydrocarbyloxides include, but are not limited to, potassium methoxide, potassium ethoxide, potassium propyloxide, potassium butoxide, and potassium pentoxide.

The reaction conditions to form these allyl alkali metal compounds are as follows. The temperature of the reaction should be between −50° C. to about 350° C., preferably 0° C. to 200° C., and most preferably 20° C. to 150° C. These temperature ranges are preferred due to such factors as the particular hydrocarbyl lithium and alkali metal hydrocarbyloxide used to form the allyl alkali metal compound and the fact that as the temperature rises the rate of reaction will also rise. The pressure that the reaction can take place at is from about atmospheric to about 10,000 psig, preferably from atmospheric to about 2,000 psig and most preferably from atmospheric to about 1,000 psig. The higher the pressure the greater the rate of the reaction. Additionally, this reaction can take place in a solvent provided the solvent is relatively inert and free of compounds which would tend to interfere with the reaction. That is, the solvent should be or substantially free of compounds which contain acid groups, water, or oxygen.

After the allyl alkali metal compound is formed it can be used either in situ or it can be separated and stored for later use. The alpha olefin and the allyl alkali metal compound can be reacted under the same conditions stated above for forming the allyl alkali metal compound. An example of an in situ process would be the addition of n-butyl lithium and potassium tert-butoxide in an access of propylene. In general, these compounds would react to yield n-butane, lithium tert-butoxide, allyl potassium, and 4-methyl-1-pentene which is a dimerization product of propylene. Additionally, some small quantities of trimers and tetramers of propylene would be formed. An example of a two-step process would be using the reactants listed above with only a slight amount of propylene. From this reaction an allyl potassium compound would precipitate from solution thereby enabling recovery of the allyl potassium from the product formed. This ally potassium can then be used with an alpha-olefin to form an addition product. Specifically, if a molar excess of propylene (for example a 10:1 molar ratio of propylene to allyl potassium) is then added to the allyl potassium, 4-methyl-1-pentene will be formed.

Regardless of how the above reaction is conducted a catalytic support can be used in the reaction also. The term "catalytic support" is defined as a composition useful in increasing the entire catalytic system's productivity and value, it is not meant to be construed as an inert composition which lends nothing to the catalytic system. A catalytic support would allow the catalyst to precipitate on and/or impregnate the catalytic support. This would provide an improved catalytic system and reaction site. Examples of catalytic supports are alkali metal carbonates; silicas, aluminas, silica-aluminas, and alumina-phosphates. These catalytic supports are broadly known in the art and are disclosed, for example, in U.S. Pat. Nos. 4,544,7901; 4,609,6371 4.656,154; 4,982,043; 4,988,6581 5,001,204; 5,021,379; and 5,026,796; which are hereby incorporated by reference.

It is preferred that the catalytic supports be alkali metal carbonates and/or silica-aluminas, for best productivity and selectivity.

EXAMPLES

These examples are provided to further assist a person skilled in the art with understanding this invention. The particular reactants, conditions, and the like, are intended to be generally illustrative of this invention and are not mean: to be construed as unduly limiting the reasonable scope of this invention.

EXAMPLE I

Preparation and Analysis of an Allyl Potassium Catalyst

In a sealed 250 mL glass bottle under anhydrous and oxygen free conditions an allyl potassium catalyst was formed. The catalyst was prepared by charging 5.6 grams of potassium t-butoxide, 65.6 grams of potassium carbonate, 100 mL of cyclohexane, and 100 mL of 2.5 molar n-butyl lithium in hexanes, to the bottle. Upon heating an orange precipitate formed. The solution was then heated to about 80° C. and after about 2 hours at this temperature, the solution was allowed to cool to 60° C. At this time propylene was pumped into the system. A reddish precipitation then occurred which seemed to coat the potassium carbonate solids. The solution was then allowed to react for about 1 hour. The precipitate was allowed to settle and the liquid was then removed. Thereafter, the precipitate was then washed 3 times will 100 mL of anhydrous cyclohexane. After each wash the precipitate was allowed to settle before the liquid was removed. The bottle was then purged with dry nitrogen and then dried at 80° C. The bottle was then allowed to cool under a nitrogen purge.

The allyl potassium catalyst isolated above was analyzed for its composition. First, 10.05 grams of the catalyst was dissolved in 40 mL of n-propanol. Second, this solution was then analyzed by an inductively coupled plasma-atomic emission spectrometer. The results obtained indicated that the sample contained 5O9o ppm potassium and 365 ppm lithium (by weight). This is equivalent to a molar ratio of 2 moles of potassium to 1 mole of lithium.

EXAMPLE II

Production of 4-Methyl-1-Pentene with the Catalysts of Example I

Approximately 56 grams of the catalyst formed above was placed in a one liter, stainless steel reactor. The reactor was then pressurized to about 1,400 psig. This pressure was maintained through the reaction. The reactor was also heated to a temperature of about 155° C. This temperature was also maintained throughout the reaction. After these pressures and temperatures were obtained, propylene was pumped into the reactor at a rate of about 5 mL per minute. A Hewlitt Packard 5890 chromatograph, equipped with a capillary column and a liquid sample valve, was attached to the reactor in order to sample the reactor effluent. The data below in Table EII represents an analysis of liquid samples taken during the reaction.

TABLE EII

| | Analysis of Liquid Samples | | | |
| --- | --- | --- | --- | --- |
| Elapsed | Weight Percent of Sample | | | |
| Time (hrs) | Propylene | 4MP1 | 4MP2 | Ratio 4MP1/4MP2 |
| 1 | 99.359 | 0.354 | 0.011 | 32 |

TABLE EII-continued

| Elapsed Time (hrs) | Analysis of Liquid Samples | | | |
|---|---|---|---|---|
| | Weight Percent of Sample | | | |
| | Propylene | 4MP1 | 4MP2 | Ratio 4MP1/4MP2 |
| 2 | 99.132 | 0.606 | 0.015 | 40 |
| 3 | 98.952 | 0.803 | 0.018 | 45 |
| 4 | 98.874 | 0.908 | 0.020 | 45 |
| 5 | 98.838 | 0.979 | 0.023 | 43 |
| 6 | 98.857 | 0.981 | 0.024 | 41 |
| 7 | 99.244 | 0.562 | 0.016 | 35 |
| 8 | 98.573 | 1.162 | 0.040 | 29 |
| 9 | 97.851 | 1.766 | 0.076 | 23 |
| 10 | 97.336 | 2.132 | 0.102 | 21 |
| 11 | 97.165 | 2.310 | 0.123 | 19 |
| 12 | 97.037 | 2.380 | 0.041 | 18 |

Note to Table EII
1) The sample taken at elapsed time equal to 7 hours is considered anomalous.
2) Weight percents do not add up to 100 because other minor products not included in Table.

It can be seen from the above data that the total propylene conversion was 2.963 weight percent. This gives a 4-methyl-1-pentene product to propylene converted ratio of about 80% (2.380/2.963). Furthermore, the 4-methyl-1-pentene to 4-methyl-2-pentene ratio varied from a high of 45:1 to a low of 18:1. This is especially important considering the difficulty in separating 4-methyl-1-pentene from 4-methyl-2-pentene.

That which is claimed is:

1. A process to produce an allyl alkali metal alkene addition catalyst and a single alkene addition product said process consisting essentially of contacting:
   a hydrocarbyl lithium; with
   an alkali metal hydrocarbyloxide wherein said alkali metal is selected form the group consisting of sodium, potassium, cesium, rubidium, and mixtures thereof;
   in the presence of propylene; and
   recovering said allyl alkali metal alkene addition catalyst and said single alkene addition product.

2. A process according to claim 1 wherein said contacting is carried out in the presence of a catalytic support.

3. A process according to claim 2 wherein said catalytic support is selected from the group consisting of alkali metal carbonates, silicas, aluminas, alumina-silicas, alumina-phosphates, and mixtures thereof.

4. A process according to claim 2 wherein said catalytic support consists essentially of potassium carbonate.

5. A process according to claim 1 wherein said hydrocarbyl lithium is selected from the group consisting essentially of methyl lithium, ethyl lithium, propyl lithium, butyl lithium, pentyl lithium, hexyl lithium, and mixtures thereof.

6. A process according to claim 1 wherein said alkali metal hydrocarbyloxide is selected from the group consisting essentially of potassium methoxide, potassium ethoxide, potassium propyloxide, potassium butoxide, potassium pentoxide, and mixtures thereof.

7. A process according to claim 1 wherein said contacting is carried out in the presence of at least one other alpha-olefin besides propylene.

8. A process according to claim 1 wherein said contacting takes place at a temperature between −50° C. and 350° C.

9. A process according to claim 1 wherein said single alkene addition product is 4-methyl-1-pentene.

10. A process according to claim 1 wherein said hydrocarbyl lithium is n-butyl lithium.

11. A process according to claim 1 wherein said alkali metal hydrocarbyloxide is potassium t-butoxide.

12. A process according to claim 1 wherein said contacting is carried out in the presence of at least one other alpha-olefin besides propylene wherein said alpha-olefin is selected from the group consisting of ethylene, 1-butene, isobutylene, 3-methyl-1-butene, 1-pentene, 3-methyl-1-pentene, 4-methyl-1-pentene, 1-hexene, 3-ethyl-1-hexene, 1-octane, 1-decene, and mixtures thereof.

13. A process to produce a single alkene addition product said process consisting essentially of contacting:
   a hydrocarbyl lithium; with
   an alkali metal hydrocarbyloxide wherein said alkali metal is selected from the group consisting of sodium, potassium, cesium, rubidium, and mixtures thereof;
   in the presence of a molar excess of propylene; and
   recovering said single alkene addition product.

14. A process according to claim 13 wherein said contacting is carried out in the presence of a catalytic support.

15. A process according to claim 14 wherein said catalytic support is selected from the group consisting of alkali metal carbonates, silicas, aluminas, alumina-silicas, alumina-phosphates, and mixtures thereof.

16. A process according to claim 14 wherein said catalytic support consists essentially of potassium carbonate.

17. A process according to claim 13 wherein said hydrocarbyl lithium is selected form the group consisting essentially of methyl lithium, ethyl lithium, propyl lithium, butyl lithium, pentyl lithium, hexyl lithium, and mixtures thereof.

18. A process according to claim 13 wherein said hydrocarbyl lithium is n-butyl lithium.

19. A process according to claim 13 wherein said alkali metal hydrocarbyloxide is selected from the group consisting essentially of potassium methoxide, potassium ethoxide, potassium propyloxide, potassium butoxide, potassium pentoxide, and mixtures thereof.

20. A process according to claim 13 wherein said alkali metal hydrocarbyloxide is potassium t-butoxide.

21. A process according to claim 13 wherein said contacting is carried out in the presence of at least one other alpha-olefin besides propylene.

22. A process according to claim 13 wherein said contacting is carried out in the presence of at least one other alpha-olefin besides propylene wherein said alpha-olefin is selected from the group consisting of ethylene, 1-butene, isobutylene, 3-methyl-1-butene, 1-pentene, 3-methyl-1-pentene, 4-methyl-1-pentene, 1-hexene, 3-ethyl-1-hexene, 1-octene, 1-decene, and mixtures thereof.

23. A process to produce 4-methyl-1-pentene said process consisting essentially of contacting n-butyl lithium and potassium tert-butoxide to form a first mixture followed by contacting said first mixture with a molar excess of propylene and then recovering said 4-methyl-1pentene.

24. A process to produce an allyl alkali metal alkene addition catalyst said process consisting essentially of contacting:
   a hydrocarbyl lithium; with
   an alkali metal hydrocarbyloxide wherein said alkali metal is selected from the group consisting of sodium potassium, cesium, rubidium, and mixtures thereof;

in the absence of a molar excess of propylene; and recovering said allyl alkali metal alkene addition catalyst.

25. A process according to claim 24 wherein said contacting is carried out in the presence of a catalytic support.

26. A process according to claim 25 wherein said catalytic support is selected from the group consisting of alkali metal carbonates, silicas, aluminas, alumina-silicas, alumina-phosphates, and mixtures thereof.

27. A process according to claim 25 wherein said catalytic support consists essentially of potassium carbonate.

28. A process according to claim 24 wherein said hydrocarbyl lithium is selected from the group consisting essentially of methyl lithium, ethyl lithium, propyl lithium, butyl lithium, pentyl lithium, hexyl lithium, and mixtures thereof.

29. A process according to claim 24 wherein said hydrocarbyl lithium is n-butyl lithium.

30. A process according to claim 24 wherein said alkali metal hydrocarbyloxide is selected from the group consisting essentially of potassium methoxide, potassium ethoxide, potassium propyloxide, potassium butoxide, potassium pentoxide, and mixtures thereof.

31. A process according to claim 4 wherein said alkali metal hydrocarbyloxide is potassium t-butoxide.

32. A process to produce an allyl potassium alkene addition catalyst said process consisting essentially of contacting n-butyl lithium and potassium tert-butoxide to form a first mixture followed by contacting said first mixture with propylene and then recovering said allyl potassium alkene addition catalyst.

* * * * *

UNITED STATES PATENT AND TRADEMARK OFFICE
CERTIFICATE OF CORRECTION

PATENT NO. : 5,210,361
DATED : May 11, 1993
INVENTOR(S) : Ted M. Pettijohn et al It is certified that error appears in the above-indentified patent and that said Letters Patent is hereby corrected as shown below:

On the title page, item [19], Lashier et al should read
-- Pettijohn et al--

On the title page, item [75], should read --Ted M. Pettijohn; Mark E. Lashier; Henry L. Hsieh, all of Bartlesville, Okla.

Signed and Sealed this

Twenty-fifth Day of October, 1994

Attest:

BRUCE LEHMAN

Attesting Officer        Commissioner of Patents and Trademarks